United States Patent
Kim et al.

(10) Patent No.: US 12,180,645 B2
(45) Date of Patent: Dec. 31, 2024

(54) CLOTHES CARE APPARATUS

(71) Applicant: SAMSUNG ELECTRONICS CO., LTD., Suwon-si (KR)

(72) Inventors: Woojin Kim, Suwon-si (KR); Jinbaek Kim, Suwon-si (KR); Eungryeol Seo, Suwon-si (KR); Geonung Lee, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 268 days.

(21) Appl. No.: 17/661,146

(22) Filed: Apr. 28, 2022

(65) Prior Publication Data

US 2022/0251774 A1   Aug. 11, 2022

Related U.S. Application Data

(63) Continuation of application No. PCT/KR2020/009278, filed on Jul. 15, 2020.

(30) Foreign Application Priority Data

Oct. 28, 2019   (KR) .................. 10-2019-0134572

(51) Int. Cl.
*D06F 73/00* (2006.01)
*D06F 58/10* (2006.01)
(Continued)

(52) U.S. Cl.
CPC .............. *D06F 73/00* (2013.01); *D06F 58/10* (2013.01); *A61L 2/07* (2013.01); *D06F 73/02* (2013.01)

(58) Field of Classification Search
CPC .......... D06F 73/00; D06F 58/10; D06F 73/02; A61L 2/07
See application file for complete search history.

(56) References Cited

U.S. PATENT DOCUMENTS

| | | | |
|---|---|---|---|
| 6,189,346 B1 * | 2/2001 | Chen ....................... | D06F 73/02 68/5 R |
| 2003/0126691 A1 * | 7/2003 | Gerlach .................. | D06F 58/10 8/158 |

(Continued)

FOREIGN PATENT DOCUMENTS

| | | |
|---|---|---|
| EP | 2471996 A2 | 7/2012 |
| JP | H-10235091 A | 9/1998 |

(Continued)

OTHER PUBLICATIONS

Machine translation of JP-2020103367 to Suzuki et al. (Year: 2020).*

(Continued)

*Primary Examiner* — Benjamin L Osterhout

(57) ABSTRACT

The present disclosure relates to a clothes care apparatus. The clothes care apparatus includes a main body including a clothes care compartment, a machine compartment, a steam generator provided in the machine compartment configured to generate steam, a steam injector including a steam injection nozzle configured to receive the steam from the steam generator and inject the steam into the clothes care compartment, at least one air injection hole configured to allow air to be injected into the clothes care compartment in order to change a direction of the steam injected from the steam injector, a regulation device configured to regulate a flow rate or a wind direction of the air injected from the at least one air injection hole, and a controller configured to control the regulation device and change the direction of the steam by regulating the air injected from the at least one air injection hole.

18 Claims, 17 Drawing Sheets

(51) Int. Cl.
*A61L 2/07* (2006.01)
*D06F 73/02* (2006.01)

(56) References Cited

U.S. PATENT DOCUMENTS

| | | | | |
|---|---|---|---|---|
| 2005/0223502 | A1* | 10/2005 | Kleker | D06F 17/04 |
| | | | | 68/5 R |
| 2006/0101867 | A1* | 5/2006 | Kleker | D06F 18/00 |
| | | | | 68/5 R |
| 2009/0133298 | A1* | 5/2009 | Kim | D06F 58/10 |
| | | | | 223/51 |
| 2010/0018072 | A1* | 1/2010 | Kim | D06F 58/203 |
| | | | | 62/238.7 |
| 2012/0160269 | A1* | 6/2012 | Pyo | D06F 58/44 |
| | | | | 134/25.1 |
| 2018/0334767 | A1* | 11/2018 | Kim | D06F 58/10 |
| 2021/0156071 | A1* | 5/2021 | Cho | D06F 73/02 |

FOREIGN PATENT DOCUMENTS

| | | | |
|---|---|---|---|
| JP | 2006280434 | A | 10/2006 |
| JP | 2020103367 | A * | 7/2020 |
| KR | 20060095293 | A | 8/2006 |
| KR | 101265605 | B1 | 5/2013 |
| KR | 101414634 | B1 | 8/2014 |
| KR | 101672280 | B1 | 11/2016 |
| KR | 20180037459 | A | 4/2018 |
| KR | 20190068273 | A | 6/2019 |

OTHER PUBLICATIONS

International Search Report and Written Opinion of the International Searching Authority in connection with International Application No. PCT/KR2020/009278 issued Oct. 30, 2020, 14 pages.

* cited by examiner

CLOTHES CARE APPARATUS

CROSS-REFERENCE TO RELATED APPLICATIONS

This application is a bypass continuation of International Application No. PCT/KR2020/009278, filed Jul. 15, 2020, which claims priority to Korean Patent Application No. 10-2019-0134572, filed Oct. 28, 2019, the disclosures of which are herein incorporated by reference in their entirety.

BACKGROUND

1. Field

The present disclosure relates to a clothes care apparatus, and more particularly, to a clothes care apparatus provided to inject steam into clothes.

2. Description of Related Art

A clothes care apparatus may include a clothes care compartment that is an accommodation space in which clothes are accommodated, and a steam generator for performing a refresh function such as removal of wrinkles on clothes, deodorization, and removal of static electricity from clothes and the like.

An entrance of the steam generator is located in a fixed place in the clothes care compartment, so that when steam is injected into the clothes care compartment, a steam flow in the clothes care compartment directs to a fixed injection direction. On the other hand, because several clothes support members are located in an upper portion of the clothing care compartment, clothes may be hung in various locations, and an amount of steam smeared with the clothes may vary depending on the location of the clothes being hung.

When clothes are placed in a direction of steam flow, a large amount of steam may be smeared with the clothes, but when clothes are not placed in the direction of the steam flow, a small amount of steam may only be smeared with the clothes. When a plurality of clothes is placed, the amount of steam smeared with the clothes may be different for each clothes depending on the fixed steam flow direction. Also, the steam may not be evenly smeared with the clothes due to the fixed steam flow direction. Because the amount of steam smeared with the clothes is reduced, wrinkles on the clothes may be less smooth, and the sterilization and deodorization ability may be reduced.

SUMMARY

The present disclosure is directed to providing a clothes care apparatus capable of regulating a speed and direction of steam injected from a steam injector with a simple configuration.

The present disclosure is directed to providing a clothes care apparatus capable of reducing an amount of steam smeared with clothes depending on a location where the clothes are hung.

An aspect of the present disclosure provides a clothes care apparatus including a main body including a clothes care compartment and a machine compartment, a steam generator provided in the machine compartment and configured to generate steam, a steam injector including a steam injection nozzle and configured to receive the steam from the steam generator and inject the steam into the clothes care compartment, at least one air injection hole configured to allow air to be injected into the clothes care compartment in order to change a direction of the steam injected from the steam injector, a regulation device configured to regulate a flow rate or a wind direction of the air injected from the at least one air injection hole, and a controller configured to control the regulation device and change the direction of the steam by regulating the air to be injected from the at least one air injection hole.

The at least one air injection hole may be provided adjacent to the steam injection nozzle.

The at least one air injection hole may include a first injection hole disposed adjacent to a left side of the steam injection nozzle and configured to inject the air in a rightward direction towards the steam injection nozzle, and a second injection hole disposed adjacent to a right side of the steam injection nozzle and configured to inject the air in a leftward direction towards the steam injection nozzle.

The regulation device may include a guide duct connected to the at least one air injection hole, and a fan configured to forcibly blow air into the clothes care compartment through the guide duct.

The regulation device may further include a damper rotatably provided in the guide duct to adjust an area of a flow path in the guide duct.

The at least one air injection hole may include a first injection hole disposed adjacent to a left side of the steam injection nozzle and configured to inject the air in a rightward direction towards the steam injection nozzle, and a second injection hole disposed adjacent to a right side of the steam injection nozzle and configured to inject the air in a leftward direction towards the steam injection nozzle, and the regulation device may include a first guide duct configured to guide the air to the first injection hole, and a second guide duct configured to guide the air to the second injection hole.

The regulation device may further include a damper rotatably provided between the first guide duct and the second guide duct and configured to open or close the first guide duct and the second guide duct, and the damper may be configured to rotate clockwise to open the first guide duct and rotate counterclockwise to open the second guide duct.

The clothes care apparatus may further include a sensor provided in the clothes care compartment and configured to detect a position of clothes in the clothes care compartment.

The controller may be further configured to regulate the flow rate or the wind direction of the air with the regulation device depending on information output from the sensor.

The at least one air injection hole may include a first injection hole disposed adjacent to a left side of the steam injection nozzle and configured to inject the air in a rightward direction towards the steam injection nozzle, and a second injection hole disposed adjacent to a right side of the steam injection nozzle and configured to inject the air in a leftward direction towards the steam injection nozzle, and the regulation device may include a bidirectional fan configured to rotate in a first direction to blow the air into a first guide duct and the first injection hole and to rotate in a second direction opposite the first direction to blow the air into a second guide duct and the second injection hole.

The clothes care apparatus may further include a position input device configured to receive information on a position of clothes in the clothes care compartment from a user, wherein the controller may be further configured to regulate the flow rate or the wind direction of the air with the regulation device depending on the information.

The regulation device may further include a valve connected to the at least one air injection hole.

The at least one air injection hole may include a first injection hole disposed adjacent to a left side of the steam injection nozzle and configured to inject the air in a rightward direction towards the steam injection nozzle, and a second injection hole disposed adjacent to a right side of the steam injection nozzle and configured to inject the air in a leftward direction towards the steam injection nozzle, and the clothes care apparatus may further include a first valve connected to the first injection hole and a second valve connected to the second injection hole.

The clothes care apparatus may further include an airflow inlet provided in the clothes care compartment and configured to allow the air in the clothes care compartment to be sucked, and an airflow outlet provided in the clothes care compartment and configured to allow the air to be discharged, wherein the at least one air injection hole may include the airflow outlet, and wherein the regulation device may include a wind direction regulator configured to regulate a direction of an airflow to be injected from the airflow outlet.

The wind direction regulator may include a rotation shaft and a rotation bar coupled to the rotation shaft for rotation, and the rotation bar may include a connection bar configured to connect the rotation bars to additional rotation bars.

Another aspect of the present disclosure provides a clothes care apparatus including a main body including a clothes care compartment and a machine compartment, a steam generator provided in the machine compartment and configured to generate steam, a steam injector including a steam injection nozzle and configured to receive the steam from the steam generator and inject the steam into the clothes care compartment, a first injection hole spaced apart from the steam injection nozzle and configured to inject air toward the steam injection nozzle, a second injection hole spaced apart from the steam injection nozzle and configured to inject the air toward the steam injection nozzle, the second injection hole being positioned on an opposite side of the first injection hole with the steam injection nozzle interposed therebetween, a regulation device configured to regulate a flow rate or a wind direction of air to be injected from the first and second air injection holes, and a controller configured to control the regulation device and change a direction of the steam by regulating the air to be injected from the first and second air injection holes.

The regulation device may include a guide duct connected to the first and second injection holes, and a fan configured to forcibly blow the air into the clothes care compartment through the guide duct.

The regulation device may include a damper rotatably provided in the guide duct and configured to adjust an area of a flow path in the guide duct, and may include a first guide duct configured to guide the air to the first injection hole, and a second guide duct configured to guide air to the second injection hole.

The regulation device may include a bidirectional fan configured to rotate in a first direction to blow the air into the first injection hole and rotate in a second direction opposite the first direction to blow the air into the second injection hole.

The clothes care apparatus may further include a position input device configured to receive information on a position of clothes in the clothes care compartment from a user, wherein the controller may be further configured to regulate the flow rate or the wind direction of the air with the regulation device depending on the information.

According to the present disclosure, because a direction and speed of steam injected from a steam injector to a clothes care compartment are regulated, the steam injected from the steam injector can be evenly smeared with the clothes.

According to the present disclosure, because the steam injected from the steam injector is evenly smeared with clothes, the ability to smooth wrinkles on the clothes and sterilize and deodorize the clothes can be improved.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

Figure 1:
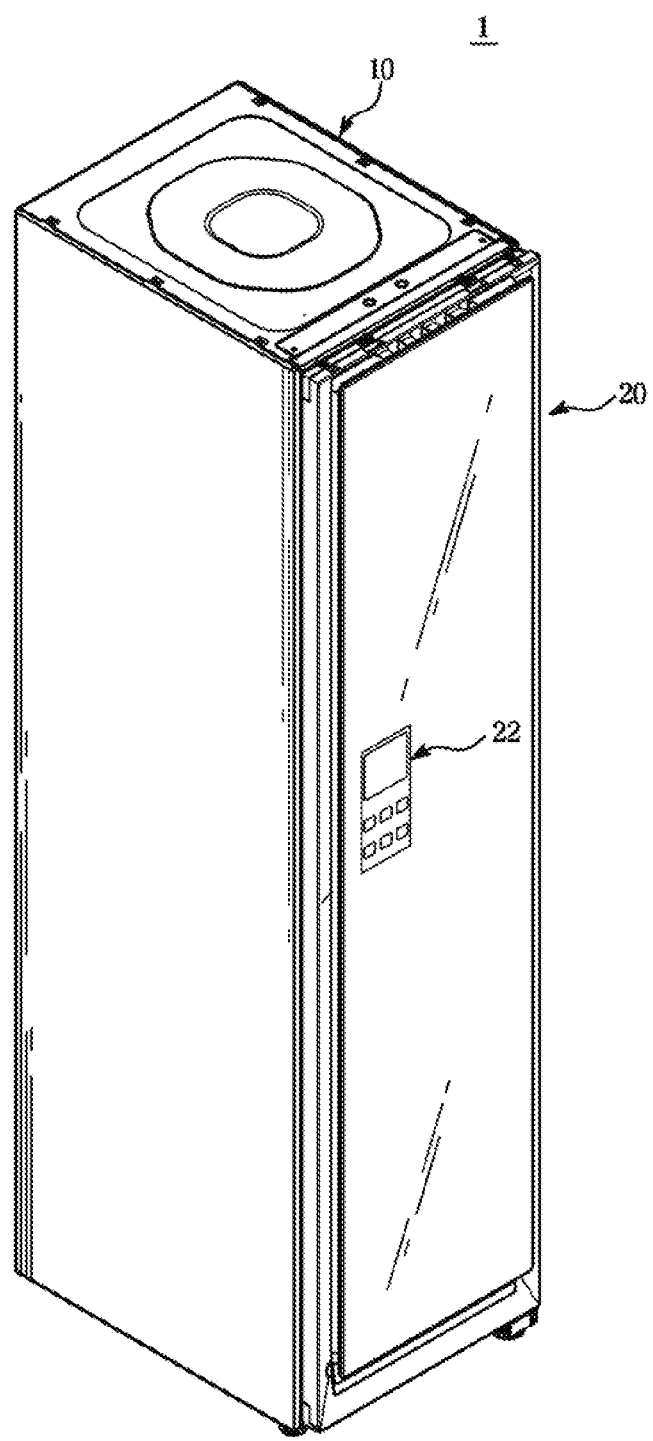
FIG. 1 illustrates a clothes care apparatus according to an embodiment of the present disclosure.

FIGS. 1 through 13, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged system or device.

The embodiments described in the present specification and the configurations shown in the drawings are examples and various modifications may be made to the embodiments and drawings of the present disclosure.

Like reference numbers or signs in the various drawings of the application represent parts or components that perform substantially the same functions.

The terms used herein are for the purpose of describing the embodiments and are not intended to restrict and/or to limit the present disclosure. For example, the singular expressions herein may include plural expressions, unless the context clearly dictates otherwise. Also, the terms "comprises" and "has" are intended to indicate that there are features, numbers, steps, operations, elements, parts, or combinations thereof described in the specification, and do not exclude the presence or addition of one or more other features, numbers, steps, operations, elements, parts, or combinations thereof.

It will be understood that, although the terms first, second, etc. may be used herein to describe various components, these components should not be limited by these terms, these terms are only used to distinguish one component from another. For example, without departing from the scope of the present disclosure, the first component may be referred to as a second component, and similarly, the second component may also be referred to as a first component. The term "and/or" includes any combination of a plurality of related items or any one of a plurality of related items.

In this specification, the terms "front," "rear," "left," and "right" used in the following description are defined with reference to the drawings, and the shape and position of each component are not limited by these terms.

Hereinafter, embodiments of the present disclosure will be described in detail with reference to the accompanying drawings.

Figure 2:
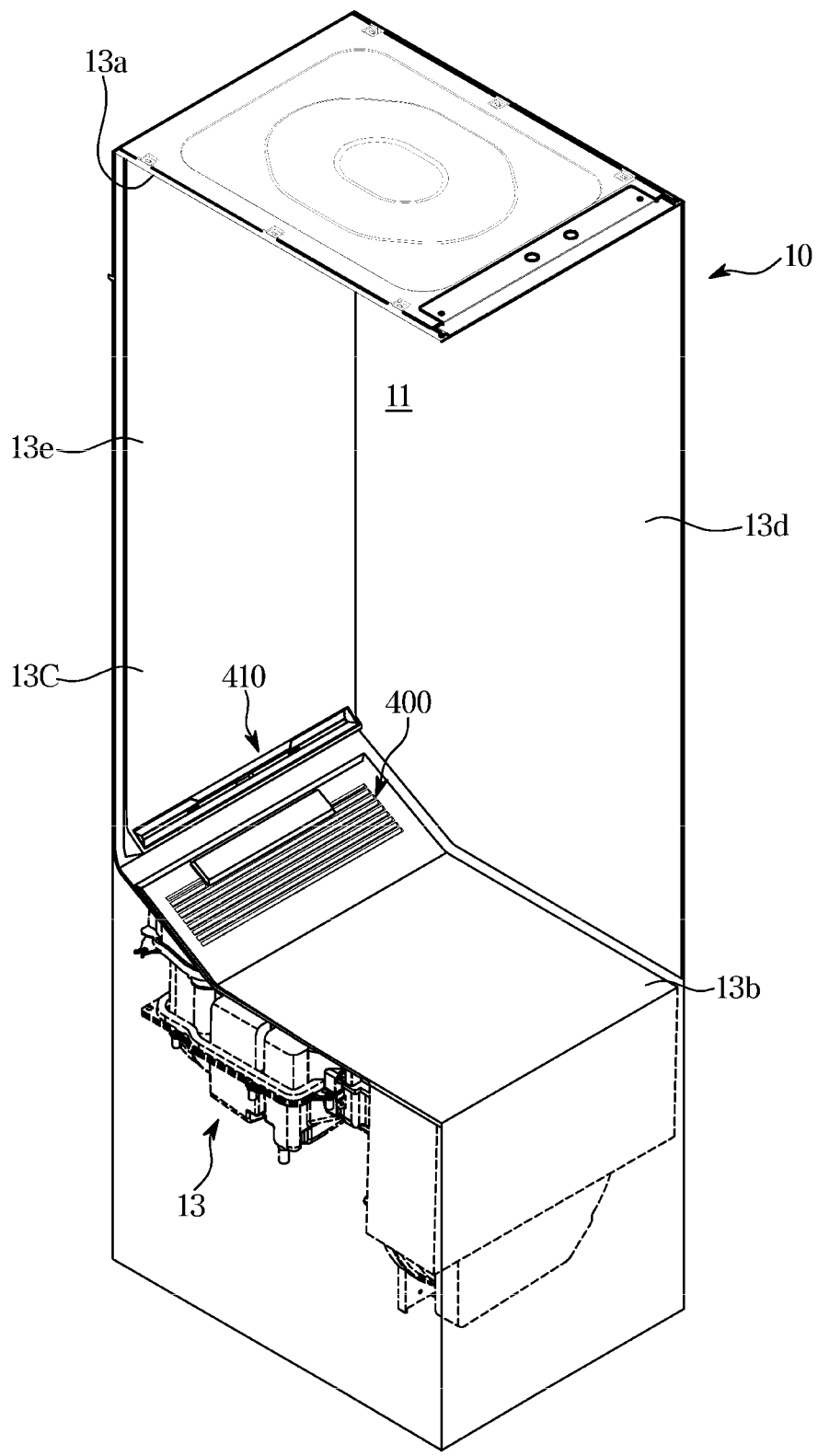
FIG. 2 illustrates an internal perspective view of the clothes care apparatus with a door separated illustrated in FIG. 1 according to an embodiment of the present disclosure.
Figure 3:
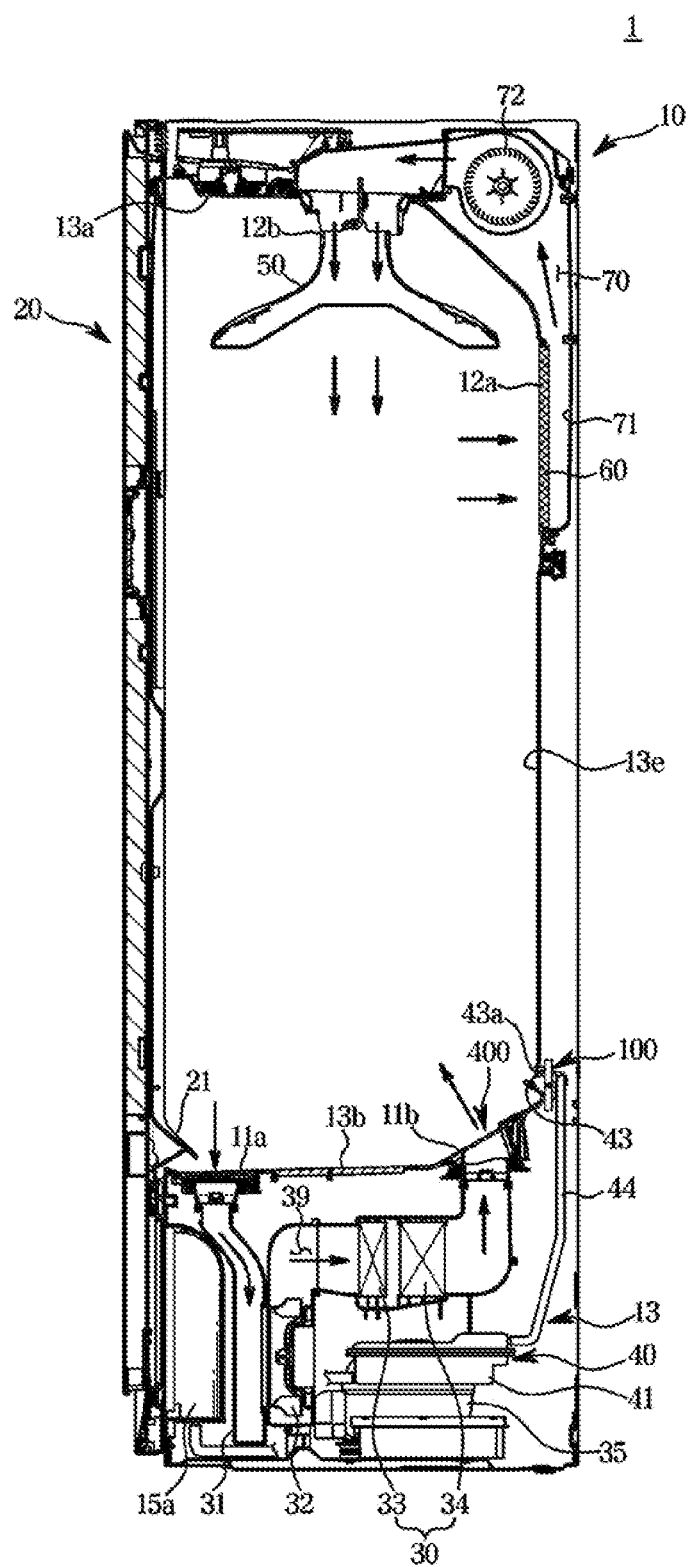
FIG. 3 illustrates a side cross-sectional view of the clothes care apparatus illustrated in FIG. 1 according to an embodiment of the present disclosure.

FIG. 1 illustrates a view illustrating a clothes care apparatus according to an embodiment of the present disclosure. FIG. 2 illustrates an internal perspective view of the clothes care apparatus with a door separated illustrated in FIG. 1 according to an embodiment of the present disclosure. FIG. 3 illustrates a side cross-sectional view of the clothes care apparatus illustrated in FIG. 1 according to an embodiment of the present disclosure.

Referring to FIGS. 1 to 3, a clothes care apparatus 1 may include a main body 10 forming an exterior, a door 20 rotatably coupled to the main body 10, and a clothes care compartment 11 provided inside the main body 10 to accommodate and care clothes. Also, the clothes care apparatus 1 may include a clothes support member 50 provided inside the clothes care compartment 11 to allow clothes to be hung, and a machine compartment 13 in which a heat exchanger 30 is provided to heat or dehumidify air inside the clothes care compartment 11, and the like. The main body 10 may include a clothes care compartment 11. Although not shown, the door 20 may be installed through a connection member such as a hinge and a link.

The clothes care compartment 11 forms a space in which clothes are accommodated. The clothes care compartment 11 may include an upper surface 13a, a lower surface 13b, a left surface 13c, a right surface 13d, and a rear surface 13e. The front of the clothes care compartment 11 is opened. Accordingly, the opening of the clothes care compartment 11 may also be opened or closed by the door 20 which opens or closes an opening of the main body 10.

The clothes care apparatus 1 may be provided with a position input device 22 to receive a position of clothes in the clothes care compartment 11 from a user. A controller 160 may regulate a flow rate of air to be injected from an air injection hole 121 in consideration of the position of the clothes depending on an input of the position input device 22. The controller 160 will be described later. Although the drawing illustrates that the position input device 22 is provided on the door 20, the present disclosure is not limited thereto, and the position input device 22 may be provided anywhere in the clothes care apparatus.

The clothes care compartment 11 forms a space in which clothes are accommodated. The clothes support member 50 may be provided inside the clothes care compartment 11 to hang and support clothes. The clothes support member 50 may be detachably mounted on an upper side of the clothes care compartment 11. One or more of the clothes support members 50 may be provided. The clothes support member 50 may be formed in the shape of a clothes hanger so that clothes may be mounted thereon. The clothes support member 50 is provided to allow air to flow therein. Dust or foreign substances attached to the clothes may be removed by the air supplied into the clothes support member 50.

The clothes care compartment 11 may include a first airflow inlet 11a and a second airflow inlet 12a, a first airflow outlet 11b and a second airflow outlet 12b, and a vapor outlet 43a. The first airflow inlet 11a and the first airflow outlet 11b may be formed on the lower surface 13b of the clothes care compartment 11. The first airflow inlet 11a may be disposed in front of the lower surface 13b of the clothes care compartment 11, and the first airflow outlet 11b may be disposed in the rear of the lower surface 13*b* of the clothes care compartment 11. The second airflow inlet 12*a* may be formed on the rear surface 13*e* of the clothes care compartment 11. The second airflow outlet 12*b* may be formed in the center of the upper surface 13*a* of the clothes care compartment 11. The second airflow inlet 12*a* and the second airflow outlet 12*b* may be disposed adjacent to each other.

A discharge grill 400 may be provided at the first airflow outlet 11*b* such that an airflow is well dispersed into the clothes care compartment 11.

The second airflow outlet 12*b* of the clothes care compartment 11 may be connected to the clothes support member 50. The air discharged through the second airflow outlet 12*b* is transferred to the clothes hung on the clothes support member 50 through an air hole (not shown) formed on the clothes support member 50.

A drain container 15*a* and a water supply container 15*b* provided to be detachable from the main body 10 may be installed at a lower portion of the main body 10. The drain container 15*a* and the water supply container 15*b* may be disposed below the clothes care compartment 11. The drain container 15*a* is provided to facilitate condensed water treatment. The water supply container 15*b* stores water used to generate steam in the steam generator 40, which will be described later. Water in the water supply container 15*b* is supplied to the steam generator 40 to generate steam. The water supply container 15*b* may be installed to be detachable from the main body 10 to easily replenish water.

The drain container 15*a* and the water supply container 15*b* may be provided in front of the machine compartment 13. The machine compartment 13 is provided on a lower side of the main body 10. The machine compartment 13 is provided below the clothes care compartment 11. The machine compartment 13 may include the heat exchanger 30 provided to dehumidify and heat air inside the clothes care compartment 11 as necessary.

Inside the machine compartment 13, a blowing fan 32, the heat exchanger 30 and the steam generator 40 may be disposed.

The heat exchanger 30 is installed to supply hot air into the clothes care compartment 11. The heat exchanger 30 is provided with an evaporator 33, a compressor 35, and a condenser 34 through which a refrigerant circulates, and is provided to dehumidify and heat air.

As the refrigerant evaporates in the evaporator 33 of the heat exchanger 30, latent heat of ambient air is absorbed, and moisture in the air is condensed and removed. Also, as the latent heat is released toward the ambient air when the refrigerant condenses in the condenser 34 via the compressor 35, the ambient air is heated. That is, the evaporator 33 and the condenser 34 function as a heat exchanger, so that the air introduced into the machine compartment 13 by the blowing fan 32 is dehumidified and heated by passing through the evaporator 33 and the condenser 34 sequentially.

The heat exchanger 30 installed in the machine compartment 13 includes a first duct 31 to connect the evaporator 33, the condenser 34 and the blowing fan 32, and the first duct 31 may be connected to the clothes care compartment 11 to form a first circulation flow path 39 to circulate air through the clothes care compartment 11 and the first duct 31. Some of the above components may be omitted.

The first duct 31 may be connected to the first airflow inlet 11*a* and the first airflow outlet 11*b* of the clothes care compartment 11. Air in the clothes care compartment 11 is introduced into the first duct 31 through the first airflow inlet 11*a*, and the introduced air is dehumidified and then discharged back to the clothes care compartment 11 through the first airflow outlet 11*b*.

The first duct 31 is provided to dehumidify the air introduced through the first airflow inlet 11*a* and discharge the dehumidified air to the first airflow outlet 11*b*. The blowing fan 32 is provided on the first duct 31 to suck air in the clothes care compartment 11 into the first duct 31.

Air in the clothes care compartment 11 may be introduced into the first circulation flow path 39 through the first airflow inlet 11*a*. The introduced air passes through the heat exchanger 30 to be dehumidified and heated, and the dehumidified and heated air may be discharged back to the clothes care compartment 11 through the first airflow outlet 11*b*.

The steam generator 40 may be disposed in the machine compartment 13. The steam generator 40 may generate steam by receiving water from the water supply container 15*b* in the machine compartment 13.

The steam generator 40 may include a steam generating part 41 connected to the water supply container 15*b* to receive water and generate steam, and a steam supply pipe 44 provided to guide the generated steam to the steam injector 100, which will be described later. The steam injector 100 may be disposed at a lower portion of the rear surface of the clothes care compartment 11. A heater (not shown) may be installed inside the steam generating part 41 to heat water.

A steam injector installing part 43 provided to install the steam injector 100 may be provided on the rear side of the clothes care compartment 11. The steam injector installing part 43 may be formed on at least a portion of the rear surface of the clothes care compartment 11. The steam injector installing part according to an embodiment of the present disclosure is exemplified to be formed on at least a portion of the rear surface of the clothes care compartment 11, but the present disclosure is not limited thereto. For example, the steam injector installing part may be assembled by forming a separate bracket. The steam injector installing part 43 may include the vapor outlet 43*a*.

The door 20 may include a door guide 21 provided to guide the movement of condensed water. The door guide 21 is provided to guide the condensed water formed by condensing on a rear surface of the door 20. The door guide 21 may be formed to be inclined downwardly from the rear surface of the door 20 toward the clothes care compartment 11. The condensed water introduced through the first airflow inlet 11*a* may be moved to the drain container 15*a* by a connection member (not shown).

The clothes care compartment 11 may include a blower 72 provided to flow air therein. The clothes care compartment 11 includes a second duct 71, and the blower 72 may be installed inside the second duct 71. The second duct 71 is provided to communicate with the clothes care compartment 11 so that a second circulation flow path 70 to circulate air through the clothes care compartment 11 and the second duct 71 may be formed. The blower 72 may be disposed on the second circulation flow path 70. The second duct 71 may be formed in the rear of the second airflow inlet 12*a* of the clothing care compartment 11. The second duct 71 is provided on an upper side of the rear surface of the clothing care compartment 11 and may include a filter member 60 therein.

The second duct 71 may be connected to the second airflow inlet 12*a* and the second airflow outlet 12*b* of the clothes care compartment 11. The second airflow outlet 12*b* is connected to the clothes support member 50 so that air in the second duct 71 is transferred to the clothes support member 50.

The blower 72 disposed inside the second duct 71 is provided to suck air in the clothes care compartment 11 through the second airflow inlet 12a to discharge to a second duct outlet 71a and the second airflow outlet 12b.

When air in the clothes care compartment 11 is introduced into the second duct 71, the air may be filtered by the filter member 60 of the second airflow inlet 12a. Dust and odors may be removed from the air introduced into the second duct 71 by the filter member 60.

When taking care of clothes, the clothes care compartment 11 is operated in a state in which the clothes are hung on the clothes support member 50 and the door 20 is closed. In this case, the air in the clothes care compartment 11 may be circulated along the first circulation flow path 39 and the second circulation flow path 70.

A first guide 410 may be provided at the lower portion of the rear surface of the clothes care compartment 11. A second guide (not shown) may be provided on the left side of the rear surface of the clothes care compartment 11, and a third guide (not shown) may be provided on the right side of the rear surface of the clothes care compartment 11. The drawing illustrates that the air injection hole 121 and a steam injection nozzle 110 are provided on the first guide 410, but is not limited thereto, and the second guide and the third guide may also be provided with the air injection hole 121 and the steam injection nozzle 110.

Figure 4:
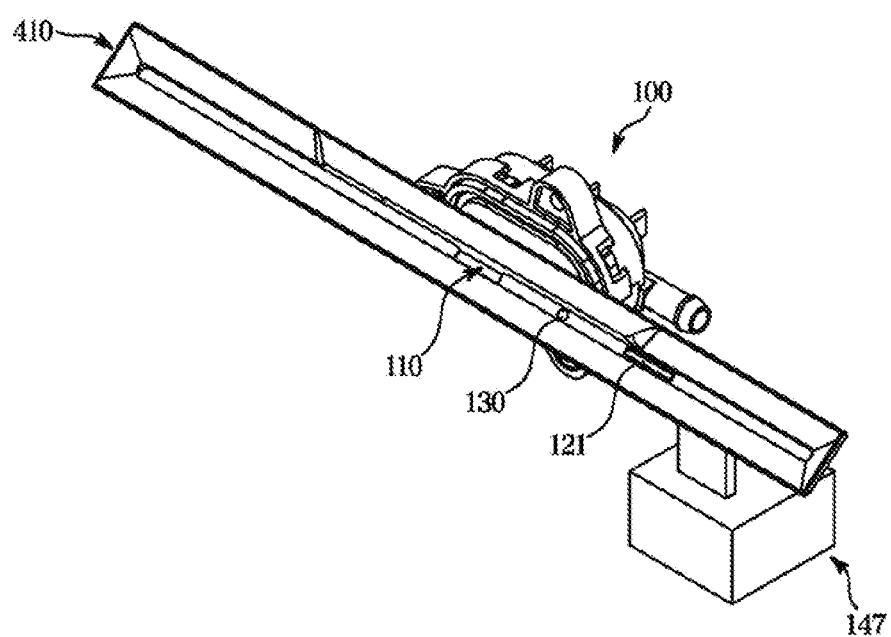
FIG. 4 illustrates a steam injector and a portion of a first guide of the clothes care apparatus illustrated in FIG. 1 according to an embodiment of the present disclosure.
Figure 5:
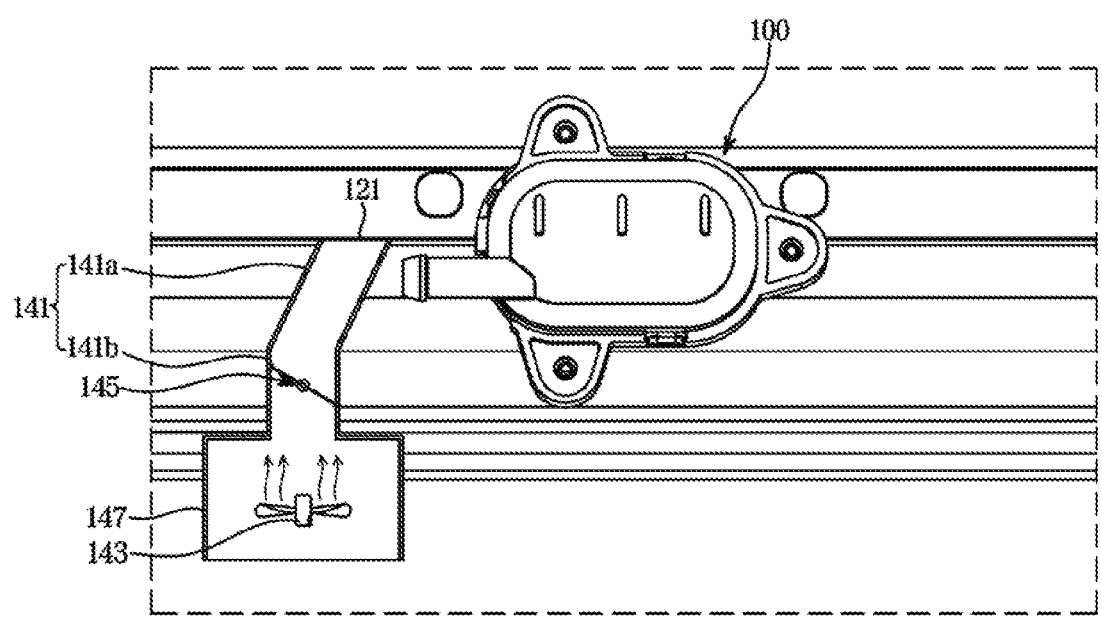
FIG. 5 illustrates a rear side of a steam injector and a flow rate regulator of the clothes care apparatus illustrated in FIG. 1 according to an embodiment of the present disclosure.
Figure 6A:
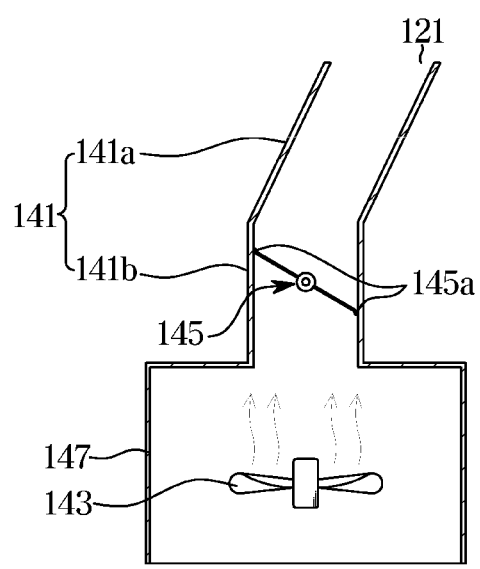
FIGS. 6A, 6B, and 6C illustrate enlarged views of the flow rate regulator according to an embodiment of the present disclosure.
Figure 6B:
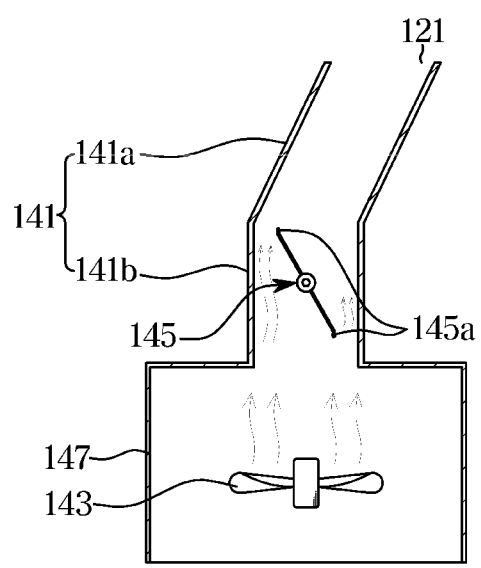
Figure 6C:
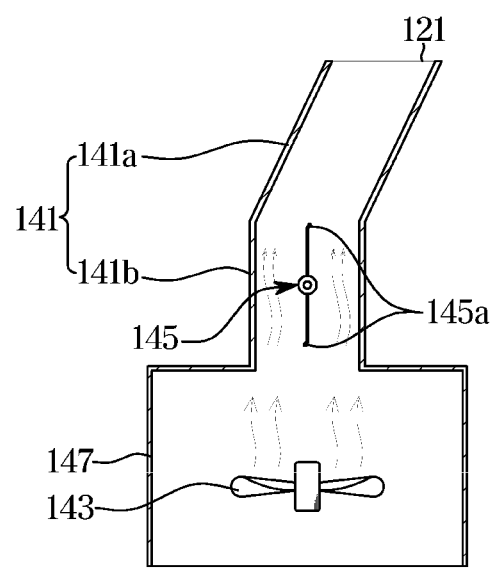

FIG. 4 illustrates a view illustrating a steam injector and a portion of a first guide of the clothes care apparatus illustrated in FIG. 1 according to an embodiment of the present disclosure. FIG. 5 illustrates a view illustrating a rear side of a steam injector and a flow rate regulator of the clothes care apparatus illustrated in FIG. 1 according to an embodiment of the present disclosure. FIGS. 6A-6C illustrate enlarged views of the flow rate regulator according to an embodiment of the present disclosure.

A description of the content overlapping with the above description will be omitted below.

Referring to FIGS. 4 to 6C, the steam injector 100, the air injection hole 121 provided to change a direction of the steam injected from the steam injector 100, and a regulation device 120 provided to regulate the flow rate of air to be injected from the air injection hole 121 may be disposed on a lower rear side of the clothes care compartment 11. The regulation device 120 may include the flow rate regulator 140.

The air injection hole 121 and the steam injection nozzle 110 may be provided on the first guide 410.

The steam injector 100 may be provided to inject steam supplied from the steam generator 40 into the clothes care compartment 11. The steam injector 100 may include the steam injection nozzle 110 provided to inject steam into the clothes care compartment 11.

The steam injection nozzle 110 and the air injection hole 121 may be provided to direct to the clothes support member 50 of the clothes care compartment 11 on which the clothes are hung. The steam injection nozzle 110 and the air injection hole 121 may be formed to inject steam toward the upper surface 13a of the clothes care compartment 11.

The steam injection nozzle 110 may be formed such that steam is widely injected. The steam injection nozzle 110 may be formed such that a size of an opening thereof increases in a direction in which the steam is injected.

The flow rate regulator 140 may include a fan 143 provided in the rear of the air injection hole 121 to forcibly blow air into the clothes care compartment 11, the air injection hole 121 provided on the rear surface 13e of the clothes care compartment 11 to inject steam in a desired direction, and a guide duct 141 provided to guide wind generated by the fan 143 to the air injection hole 121. Some of the above components may be omitted. FIGS. 4 and 5 illustrate that the fan 143, the guide duct 141, and the air injection hole 121 are provided one by one, but is not limited thereto, and one or more may be provided.

The guide duct 141 may include a first portion 141a bent toward the air injection hole 121 and a second portion 141b extending toward the upper surface 13a of the clothes care compartment 11.

Steam injected from the steam injection nozzle 110 may be injected in a desired direction due to the air injection hole 121. As illustrated in FIG. 5, because the air injection hole 121 disposed on the left side of the steam injection nozzle 110 when viewed from the rear surface 13e of the clothes care compartment 11 causes air to be injected toward the right side of the steam injection nozzle 110, steam may be sent in the right direction. The flow rate regulator 140 may regulate the flow rate of air supplied to the air injection hole 121 to smoothly change the direction of steam.

FIG. 5 illustrates that an end of the guide duct 141 directs to the right side, but the present disclosure is not limited thereto. When the guide duct 141 is provided to direct to a point between the upper surface 13a and the front surface of the clothes care apparatus 1 and air is strongly injected, steam may be sent to the left side.

The air injection hole 121 may be provided adjacent to the steam injection nozzle 110. Due to this, the direction of the steam may be changed more smoothly.

The flow rate regulator 140 may smoothly supply air to the air injection hole 121 through the guide duct 141 and the fan 143.

The flow rate regulator 140 may include a damper 145 rotatably provided in the guide duct 141. The damper 145 may regulate the flow rate of air supplied to the air injection hole 121 by adjusting a flow path area in the guide duct 141.

The damper 145 may include an impact buffer member 145a in order to reduce an impact upon collision with the guide duct 141. The impact buffer member 145a may include rubber. The damper 145 may be provided using a step motor.

The clothes care apparatus may further include a sensor 130 provided to detect a position of clothes in the clothes care compartment 11, and the controller 160 provided to regulate the flow rate of air to be injected from the air injection hole 121 depending on an output of the sensor 130.

The sensor 130 may detect clothes accommodated in the clothes care compartment 11 and provide information on the number of the clothes to the controller 160. Also, the sensor 130 may detect a position of the clothes accommodated in the clothes care compartment 11 and provide detection information to the controller 160. The controller 160 may regulate the flow rate of air injected from the air injection hole 121 depending on information output from the sensor 130.

The drawing illustrates that the sensor 130 is provided at the lower part of the rear surface 13e of the clothes care compartment 11 to be disposed between the air injection hole 121 and the steam injection nozzle, but the present disclosure is not limited thereto, and the sensor may be freely disposed on the upper surface 13a, the lower surface 13b, the left surface 13c, and the right surface 13d of the clothes care compartment 11.

Various sensors for recognizing clothes accommodated in the clothes care compartment 11 may be used as the sensor 130. For example, the sensor 130 may include a proximity sensor, an infrared sensor (IR sensor), an ultrasonic sensor, an optical sensor, or a switching sensor. However, the present disclosure is not limited thereto.

FIG. 6A illustrates a case in which the damper 145 completely closes the guide duct 141, and air is not supplied to the air injection hole 121. FIG. 6B illustrates a case in which the damper 145 partially closes the guide duct 141, and more air is supplied than in a case in which the guide duct 141 is closed with the air injection hole 121. FIG. 6C illustrates a case in which the damper 145 completely opens the guide duct 141, and most of air generated from the fan is supplied to the air injection hole 121. Through these, the flow rate of air to be supplied to the air injection hole 121 is regulated, so that the direction of steam to be injected may be regulated.

Figure 7:
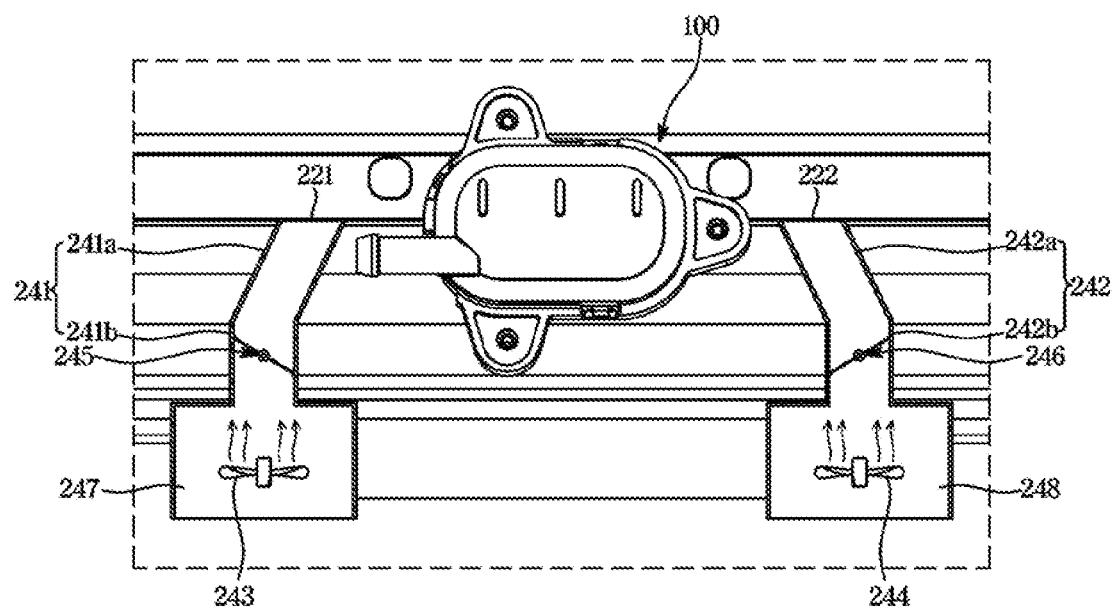
FIG. 7 illustrates a flow rate regulator according to another embodiment of the present disclosure.

FIG. 7 illustrates a flow rate regulator according to another embodiment of the present disclosure.

A description of the content overlapping with the above description will be omitted below.

Referring to FIG. 7, an air injection hole may include a first injection hole 221 disposed adjacent to the left side of the steam injection nozzle 110 to inject air in the direction of the right surface 13d of the clothes care compartment 11 toward the steam injection nozzle 110, and a second injection hole 222 disposed adjacent to the right side of the steam injection nozzle 110 to inject air in the direction of the left surface 13c of the clothes care compartment 11 toward the steam injection nozzle 110.

A flow rate regulator 240 may include a first guide duct 241, a first fan 243, a second guide duct 242, a second fan 244, a first damper 245, a second damper 246, a first case 247, and a second case 248. Some of the above components may be omitted.

A direction of steam may be changed in a desired direction due to the first injection hole 221 and the second injection hole 222 as described above.

The flow rate regulator 240 may smoothly supply air to the first injection hole 221 through the first guide duct 241 and the first fan 243. Also, the flow rate regulator 240 may smoothly supply air to the second injection hole 222 through the second guide duct 242 and the second fan 244.

The guide ducts 241 and 242 may include a first portion 241a bent toward the air injection holes 221 and 222, and a second portion 241b extending toward the upper surface 13a of the clothes care compartment 11.

Figure 8A:
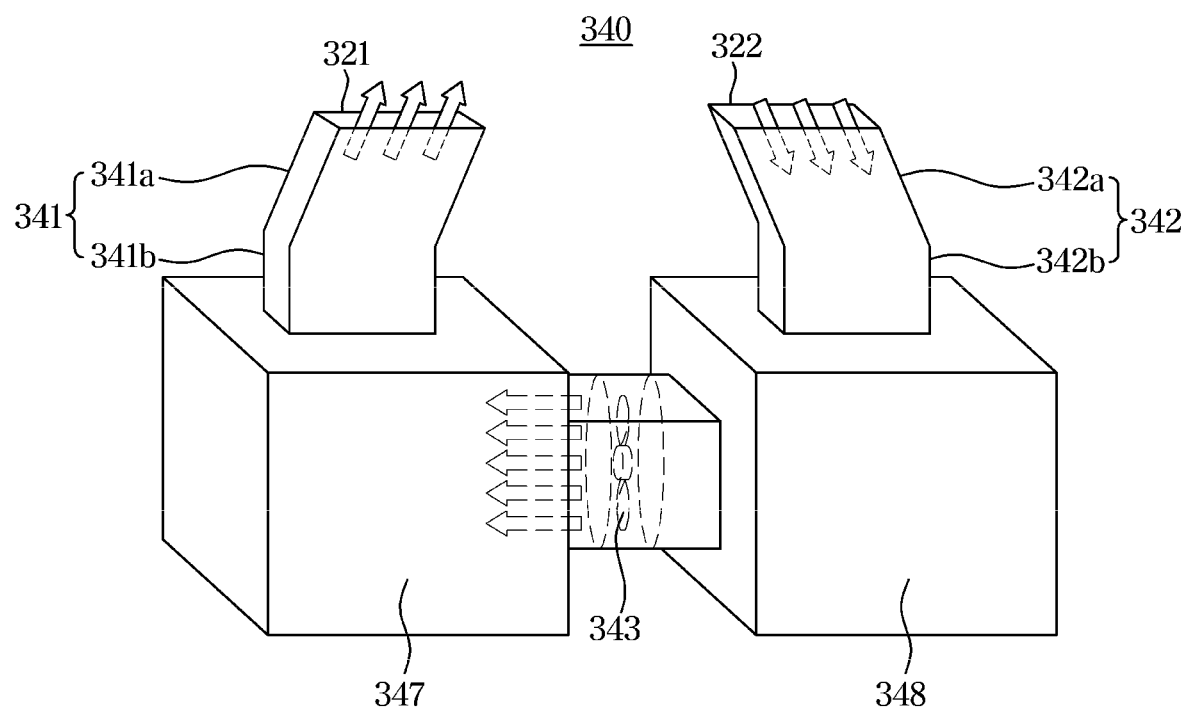
FIGS. 8A and 8B illustrate a flow rate regulator according to another embodiment of the present disclosure.
Figure 8B:
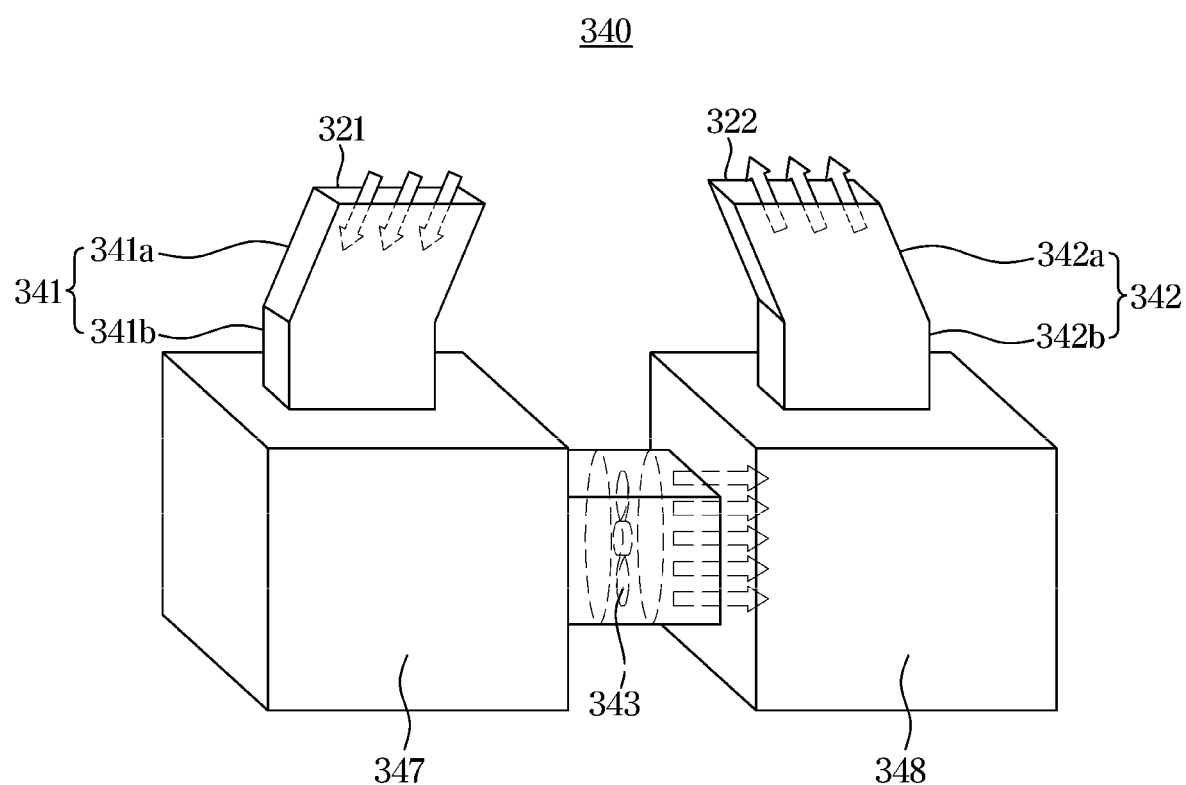

FIGS. 8A and 8B illustrate a flow rate regulator according to another embodiment of the present disclosure.

Referring to FIGS. 8A and 8B, a flow rate regulator 340 may include a first guide duct 341, a second guide duct 342, a bidirectional fan 343, a first case 347, and a second case 348. The bidirectional fan 343 may be provided between the first case 347 and the second case 348. Some of the above components may be omitted.

As illustrated in FIG. 8A, the bidirectional fan 343 may rotate in one direction to blow air to be injected to the first guide duct 341 in order to change the direction of steam. Air discharged from the first guide duct 341 to a first injection hole 321 may be recovered to the second guide duct 342 through a second injection hole 322.

As illustrated in FIG. 8B, the bidirectional fan 343 may rotate in the opposite direction to blow air to be injected to the second guide duct 342 in order to change the direction of steam. Air discharged from the second guide duct 342 to the second injection hole 322 may be recovered to the first guide duct 341 through the first injection hole 321.

Accordingly, air may be blown to both the first injection hole 321 and the second injection hole 322 by a single fan.

The guide ducts 341 and 342 may include a first portion 341a bent toward the air injection holes 321 and 322, and a second portion 341b extending toward the upper surface 13a of the clothes care compartment 11.

Figure 9:
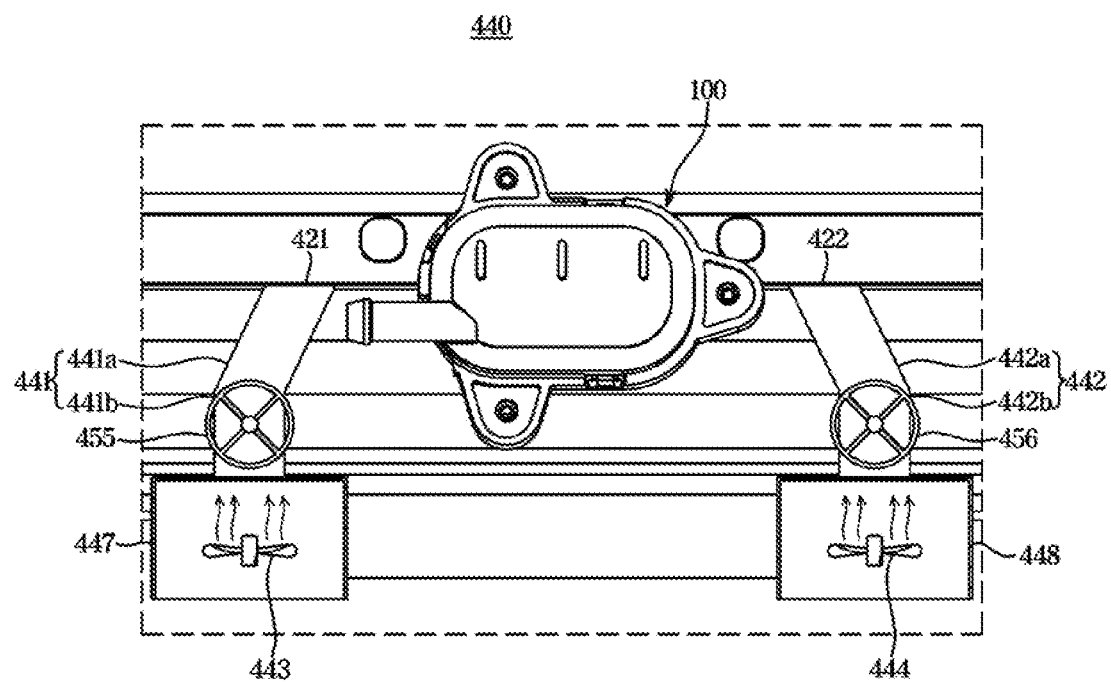
FIG. 9 illustrates a flow rate regulator according to another embodiment of the present disclosure.

FIG. 9 illustrates a view illustrating a flow rate regulator according to another embodiment of the present disclosure.

Referring to FIG. 9, a flow rate regulator 440 may further include a valve connected to an air injection hole. The valve may be provided in the rear of a first guide 410. The flow rate regulator 440 may include a first valve 455, a first fan 443, a first casing 447, a second valve 456, a second fan 444, and a second casing 448. Some of the above components may be omitted. Although the drawing illustrates that two valves are provided, the present disclosure is not limited thereto, and one or more valves may be provided.

The flow rate regulator 440 may regulate the flow rate of air to be supplied to the air injection hole using the valves 455 and 456 regardless of the power of the fans 443 and 444. For example, the flow rate regulator 440 may regulate the flow rate of air to be supplied to a first injection hole 421 by opening or closing the first valve 455 regardless of the power of the first fan 443. Also, the flow rate regulator 440 may regulate the flow rate of air to be supplied to a second injection hole 422 by opening or closing the second valve 456 regardless of the power of the second fan 444.

Guide ducts 441 and 442 may include a first portion 441a bent toward the air injection holes 421 and 422, and a second portion 441b extending toward the upper surface 13a of the clothes care compartment 11.

Figure 10A:
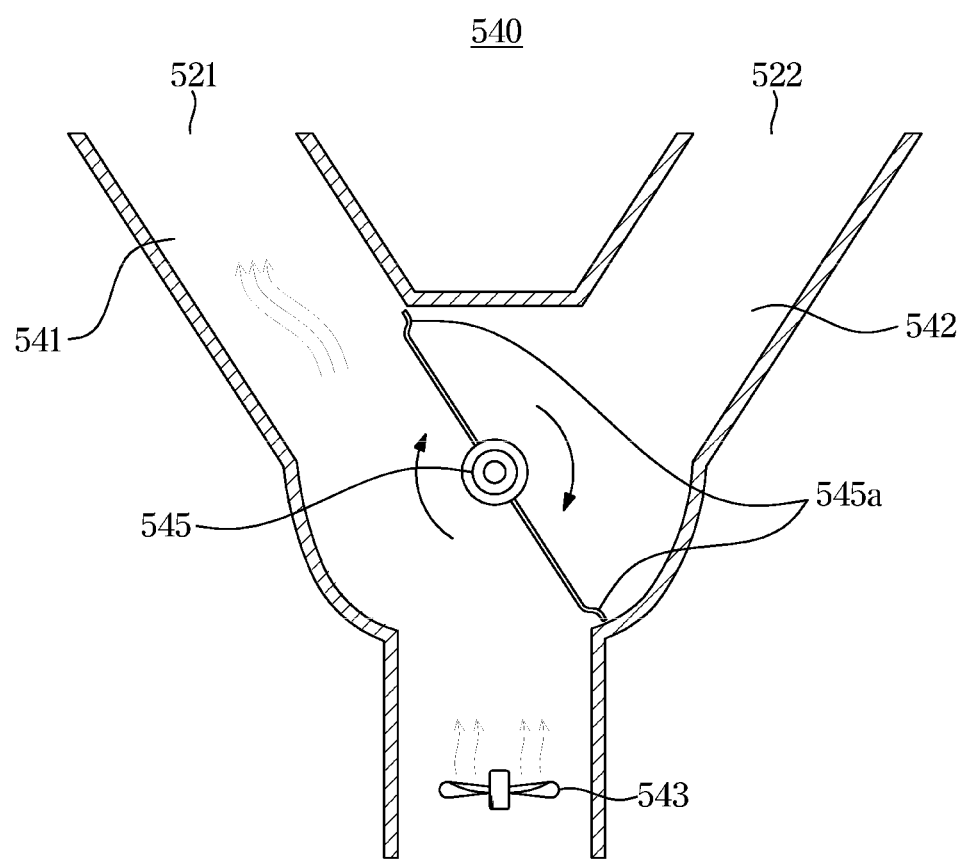
FIGS. 10A and 10B illustrate a flow rate regulator according to another embodiment of the present disclosure.
Figure 10B:
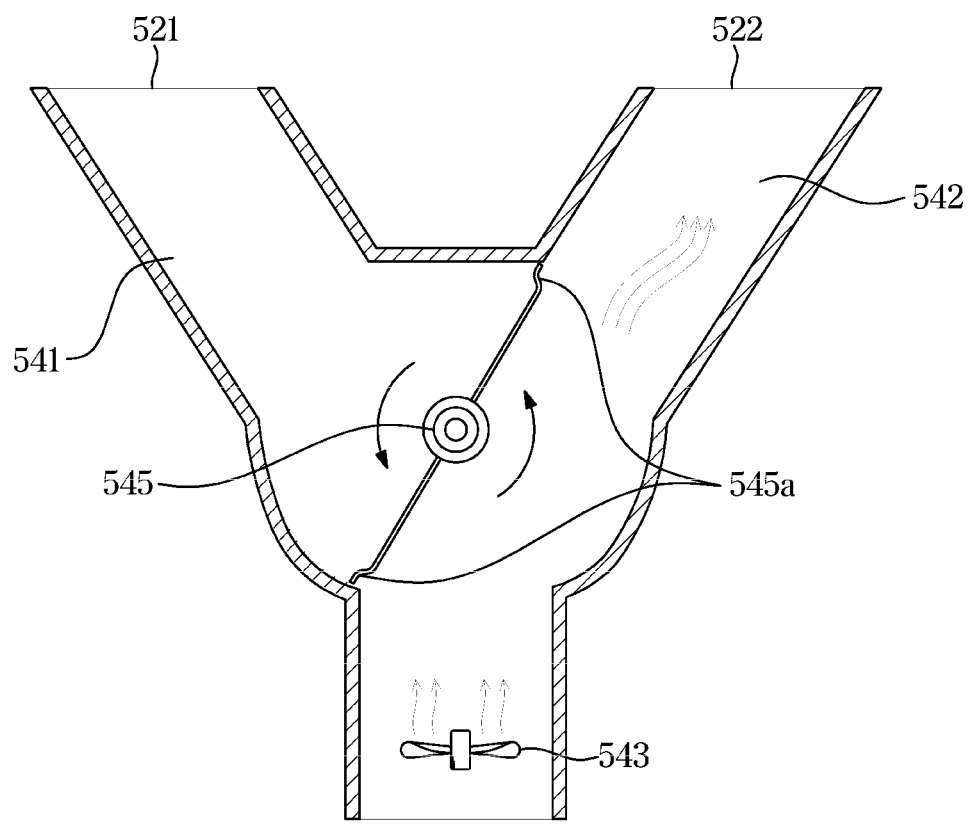

FIGS. 10A and 10B illustrate a flow rate regulator according to another embodiment of the present disclosure.

Referring to FIGS. 10A and 10B, a flow rate regulator 540 may further include a damper 545 rotatably provided between guide ducts 541 and 542 to open or close the first guide duct 541 and the second guide duct 542.

The flow rate regulator 540 may further include a first guide duct 541 provided to guide air to a first injection hole 521 and a second guide duct 542 provided to guide air to a second injection hole 522. Some of the above components may be omitted.

As illustrated in FIG. 10A, as the damper 545 rotates clockwise to open the first guide duct 541, air may be supplied to the first injection hole 521. As illustrated in FIG. 10B, as the damper 545 rotates counterclockwise to open the second guide duct 542, air may be supplied to the second injection hole 522. When the damper 545 does not rotate and is in a neutral position, the flow of air may be stopped. The neutral position refers to a damper position when there is no flow rate introduced into the first guide duct 541 and the second guide duct 542.

The damper 545 may include an impact buffer member 545a in order to reduce an impact upon collision with a flow path. The impact buffer member 545a may include rubber.

Figure 11:
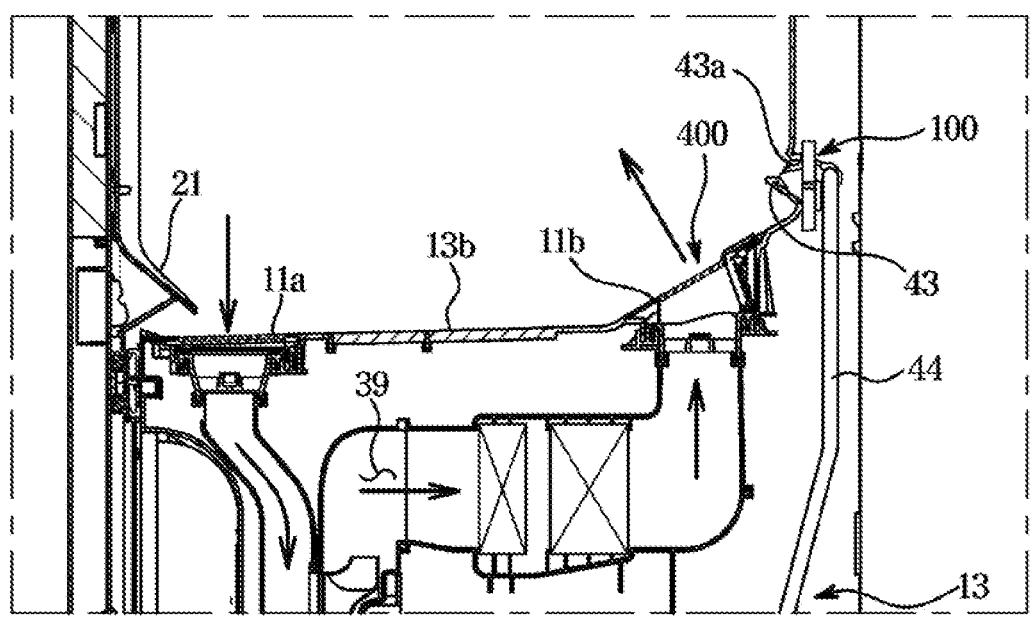
FIG. 11 illustrates an enlarged view of a part of a clothes care apparatus according to another embodiment of the present disclosure.
Figure 12:
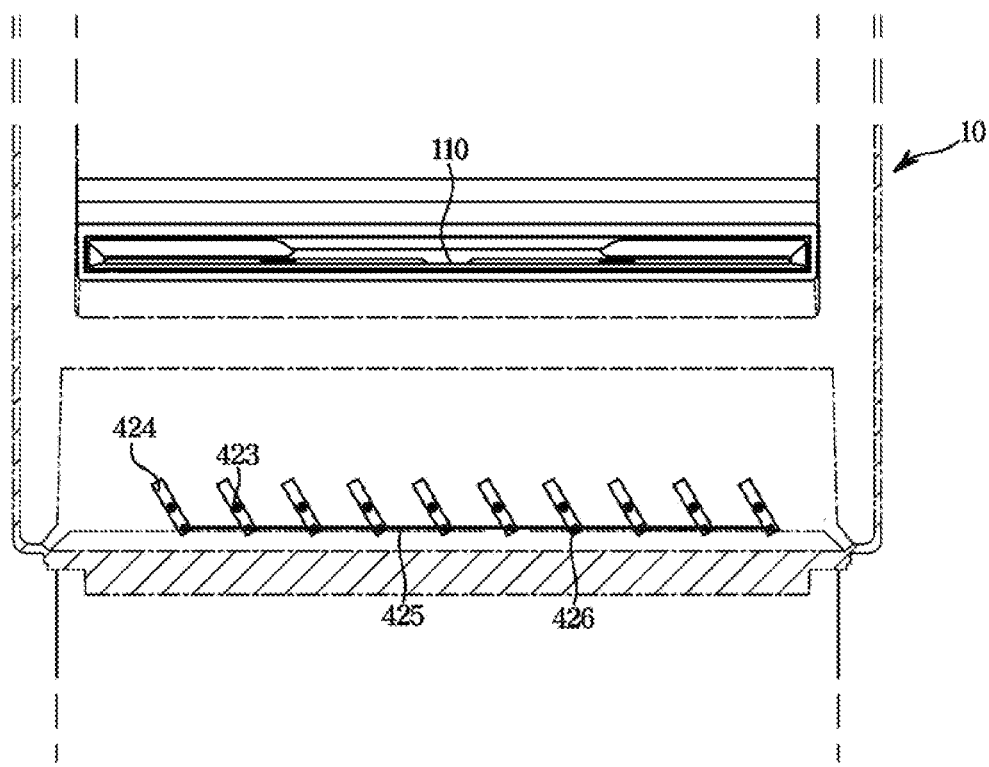
FIG. 12 illustrates an enlarged view of a wind direction regulator according to another embodiment of the present disclosure.

FIG. 11 illustrates an enlarged view of a part of a clothes care apparatus according to another embodiment of the present disclosure. FIG. 12 illustrates an enlarged view of a wind direction regulator according to another embodiment of the present disclosure.

Referring to FIGS. 11 and 12, the clothes care apparatus 1 may further include a wind direction regulator 420 provided to regulate a direction of steam using wind directions of the airflow inlet and the airflow outlet in the clothes care compartment 11. The regulation device 120 may include the wind direction regulator 420.

As described above, the air introduced into the first airflow inlet 11a passes through the first airflow outlet 11b through the first duct 31 and the first circulation flow path 39 and is discharged through the discharge grill 400. The wind direction regulator 420 may be configured to regulate a direction of airflow to be injected from the first airflow outlet 11b. Some of the above components may be omitted.

The wind direction regulator 420 may be provided adjacent to the rear surface 13e of the clothes care compartment 11. In this case, the airflow inlet may include the first airflow inlet 11a, and the airflow outlet may include the first airflow outlet 11b.

FIG. 12 is a view schematically illustrating the wind direction regulator 420 from the front of the clothes care apparatus 1, and the discharge grill 400 is omitted. The wind direction regulator 420 may include a rotation shaft 423, a rotation bar 424 rotatably coupled to the rotation shaft 423, and a connection bar 425 to connect the rotation bar 424. The rotation bar 424 may include a connection shaft 426. The rotation shaft 423 may be configured as a step motor. Some of the above components may be omitted.

The rotation shaft 423 may rotate to rotate the rotation bar 424, and the other rotation bar 424 may be rotated through the connection bar 425 connected to the connection shaft 426. The at least one rotation shaft 423 may rotate to rotate the one or more rotation bars 424.

The wind direction regulator 420 may regulate the direction of steam through a simple configuration without adding a complicated configuration.

Figure 13:
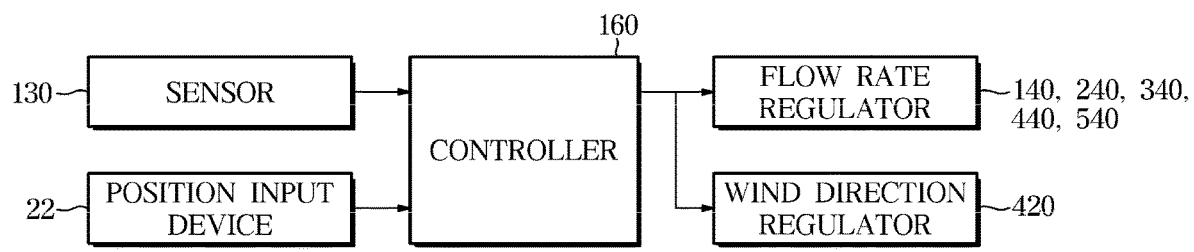
FIG. 13 illustrates a block diagram of a control flow according to an embodiment of the present disclosure.

FIG. 13 illustrates a block diagram of a control flow according to an embodiment of the present disclosure.

Referring to FIG. 13, the controller 160 may rotate the flow rate regulators 140, 240, 340, 440 and 540, and the wind direction regulator 420. The user may set information on the position of the clothes in the controller 160 using the position input device 22, and may control the flow rate regulators 140, 240, 340, 440 and 540, and the wind direction regulator 420. In addition, the sensor 130 provided in the clothes care compartment 11 measures the position of the clothes, so that the controller 160 may receive information on the clothes or may control the flow rate regulators 140, 240, 340, 440 and 540, and the wind direction regulator 420. Some of the above components may be omitted.

The foregoing has illustrated and described specific embodiments. However, it should be understood by those of skilled in the art that the disclosure is not limited to the above-described embodiments, and various changes and modifications may be made without departing from the technical idea of the disclosure described in the following claims.

Although the present disclosure has been described with various embodiments, various changes and modifications may be suggested to one skilled in the art. It is intended that the present disclosure encompass such changes and modifications as fall within the scope of the appended claims.

What is claimed is:

1. A clothes care apparatus comprising:
a main body comprising a clothes care compartment and a machine compartment;
a steam generator provided in the machine compartment and configured to generate steam;
a steam injector comprising a steam injection nozzle and configured to receive the steam from the steam generator and inject the steam into the clothes care compartment;
at least one air injection hole configured to allow air to be injected into the clothes care compartment in order to change a direction of the steam injected from the steam injector;
a regulation device configured to regulate a flow rate or a wind direction of the air injected from the at least one air injection hole and comprising a valve connected to the at least one air injection hole; and
a controller configured to control the regulation device and change the direction of the steam by regulating the air to be injected from the at least one air injection hole.

2. The clothes care apparatus according to claim 1, wherein the at least one air injection hole is provided adjacent to the steam injection nozzle.

3. The clothes care apparatus according to claim 2, wherein the at least one air injection hole comprises:
a first injection hole disposed adjacent to a left side of the steam injection nozzle and configured to inject the air in a rightward direction towards the steam injection nozzle, and
a second injection hole disposed adjacent to a right side of the steam injection nozzle and configured to inject the air in a leftward direction towards the steam injection nozzle.

4. The clothes care apparatus according to claim 1, wherein the regulation device comprises:
a guide duct connected to the at least one air injection hole, and
a fan configured to forcibly blow air into the clothes care compartment through the guide duct.

5. The clothes care apparatus according to claim 4, wherein the regulation device further comprises a damper rotatably provided in the guide duct to adjust an area of a flow path in the guide duct.

6. The clothes care apparatus according to claim 1, wherein:
the at least one air injection hole comprises:
a first injection hole disposed adjacent to a left side of the steam injection nozzle and configured to inject the air in a rightward direction towards the steam injection nozzle, and
a second injection hole disposed adjacent to a right side of the steam injection nozzle and configured to inject the air in a leftward direction towards the steam injection nozzle; and
the regulation device comprises:
a first guide duct configured to guide the air to the first injection hole, and
a second guide duct configured to guide the air to the second injection hole.

7. The clothes care apparatus according to claim 6, wherein:
the regulation device further comprises a damper rotatably provided between the first guide duct and the second guide duct, the damper configured to open or close the first guide duct and the second guide duct, and
the damper is configured to rotate clockwise to open the first guide duct and rotate counterclockwise to open the second guide duct.

8. The clothes care apparatus according to claim 1, further comprising a sensor provided in the clothes care compartment and configured to detect a position of clothes in the clothes care compartment.

9. The clothes care apparatus according to claim 8, wherein the controller is further configured to regulate the flow rate or the wind direction of the air with the regulation device depending on information output from the sensor.

10. The clothes care apparatus according to claim 1, wherein:
the at least one air injection hole comprises:
a first injection hole disposed adjacent to a left side of the steam injection nozzle and configured to inject the air in a rightward direction towards the steam injection nozzle, and
a second injection hole disposed adjacent to a right side of the steam injection nozzle and configured to inject the air in a leftward direction towards the steam injection nozzle; and
the regulation device comprises a bidirectional fan configured to:
rotate in a first direction to blow the air into a first guide duct and the first injection hole, and
rotate in a second direction opposite the first direction to blow the air into a second guide duct and the second injection hole.

11. The clothes care apparatus according to claim 1, further comprising:
a position input device configured to receive information on a position of clothes in the clothes care compartment from a user,
wherein the controller is further configured to regulate the flow rate or the wind direction of the air with the regulation device depending on the information.

12. The clothes care apparatus according to claim 1, wherein:
the at least one air injection hole comprises:
a first injection hole disposed adjacent to a left side of the steam injection nozzle and configured to inject the air in a rightward direction towards the steam injection nozzle, and
a second injection hole disposed adjacent to a right side of the steam injection nozzle and configured to inject the air in a leftward direction towards the steam injection nozzle, and
the clothes care apparatus further comprises a first valve connected to the first injection hole, and a second valve connected to the second injection hole.

13. The clothes care apparatus according to claim 1, further comprising:
an airflow inlet provided in the clothes care compartment, the airflow inlet configured to allow the air in the clothes care compartment to be sucked; and
an airflow outlet provided in the clothes care compartment, the airflow outlet configured to allow the air to be discharged,
wherein the at least one air injection hole comprises the airflow outlet, and
wherein the regulation device comprises a wind direction regulator configured to regulate a direction of an airflow to be injected from the airflow outlet.

14. The clothes care apparatus according to claim 13, wherein:
the wind direction regulator comprises a rotation shaft and a rotation bar coupled to the rotation shaft for rotation, and
the rotation bar comprises a connection bar configured to connect the rotation bar to additional rotation bars.

15. A clothes care apparatus comprising:
a main body comprising a clothes care compartment and a machine compartment;
a steam generator provided in the machine compartment and configured to generate steam;
a steam injector comprising a steam injection nozzle and configured to receive the steam from the steam generator and inject the steam into the clothes care compartment;
a first injection hole spaced apart from the steam injection nozzle and configured to inject air toward the steam injection nozzle;
a second injection hole spaced apart from the steam injection nozzle and configured to inject the air toward the steam injection nozzle, the second injection hole being positioned on an opposite side of the first injection hole with the steam injection nozzle interposed therebetween;
a regulation device configured to regulate a flow rate or a wind direction of the air to be injected from the first and second injection holes; and
a controller configured to control the regulation device and change a direction of the steam by regulating the air to be injected from the first and second injection holes,
wherein the regulation device comprises a bidirectional fan configured to rotate in a first direction to blow the air into the first injection hole and rotate in a second direction opposite the first direction to blow the air into the second injection hole.

16. The clothes care apparatus according to claim 15, wherein the regulation device comprises:
a guide duct connected to the first and second injection holes; and
a fan configured to forcibly blow the air into the clothes care compartment through the guide duct.

17. The clothes care apparatus according to claim 16, wherein the regulation device comprises:
a damper rotatably provided in the guide duct, the damper configured to adjust an area of a flow path in the guide duct;
a first guide duct configured to guide the air to the first injection hole; and
a second guide duct configured to guide air to the second injection hole.

18. The clothes care apparatus according to claim 15, further comprising:
a position input device configured to receive information on a position of clothes in the clothes care compartment from a user,
wherein the controller is further configured to regulate the flow rate or the wind direction of the air with the regulation device depending on the information.

* * * * *